US011378517B2

(12) United States Patent
Takanashi et al.

(10) Patent No.: US 11,378,517 B2
(45) Date of Patent: *Jul. 5, 2022

(54) BIOLOGICAL SUBSTANCE DETECTION METHOD

(71) Applicant: Konica Minolta, Inc., Tokyo (JP)

(72) Inventors: Kensaku Takanashi, Hachioji (JP); Hideki Goda, Tokyo (JP); Hisatake Okada, Tachikawa (JP); Yasushi Nakano, Hino (JP); Kohsuke Gonda, Sendai (JP); Motohiro Takeda, Sendai (JP); Noriaki Ohuchi, Sendai (JP)

(73) Assignee: KONICA MINOLTA, INC., Tokyo (JP)

(*) Notice: Subject to any disclaimer, the term of this patent is extended or adjusted under 35 U.S.C. 154(b) by 89 days.

This patent is subject to a terminal disclaimer.

(21) Appl. No.: 15/950,648

(22) Filed: Apr. 11, 2018

(65) Prior Publication Data

US 2018/0231466 A1    Aug. 16, 2018

Related U.S. Application Data

(63) Continuation-in-part of application No. 13/819,453, filed as application No. PCT/JP2011/069553 on Aug. 30, 2011, now Pat. No. 9,976,959.

(30) Foreign Application Priority Data

Aug. 31, 2010  (JP) .............................. JP2010-193154

(51) Int. Cl.
*G01N 21/64* (2006.01)
*G01N 33/58* (2006.01)
*G01N 33/483* (2006.01)

(52) U.S. Cl.
CPC ..... *G01N 21/6486* (2013.01); *G01N 21/6428* (2013.01); *G01N 21/6458* (2013.01); *G01N 21/6489* (2013.01); *G01N 33/4833* (2013.01); *G01N 33/582* (2013.01); *G01N 33/587* (2013.01); *G01N 2021/6439* (2013.01)

(58) Field of Classification Search
CPC ............. G01N 33/4833; G01N 33/582; G01N 2021/6441
See application file for complete search history.

(56) References Cited

U.S. PATENT DOCUMENTS

| 5,544,650 | A | 8/1996 | Boon |
| 9,976,959 | B2* | 5/2018 | Takanashi .......... G01N 21/6428 |
| 10,031,139 | B2* | 7/2018 | Takanashi ............ G01N 33/533 |
| 10,458,983 | B2* | 10/2019 | Takanashi ............ G01N 33/585 |
| 10,551,386 | B2* | 2/2020 | Takanashi .......... G01N 21/6428 |
| 2008/0293584 | A1 | 11/2008 | Aizawa |
| 2009/0141959 | A1* | 6/2009 | Can .................... G01N 21/6428 382/133 |
| 2010/0041017 | A1* | 2/2010 | Tsukada ............. G01N 21/6489 435/5 |
| 2010/0304403 | A1 | 12/2010 | Roby |
| 2011/0129932 | A1 | 6/2011 | Jones |

FOREIGN PATENT DOCUMENTS

| JP | 2009115599 A | 5/2009 |
| JP | 2009540318 A | 11/2009 |
| JP | 2009281760 A | 12/2009 |
| JP | 2010134195 A | 6/2010 |
| WO | 99/288856 A1 | 6/1999 |
| WO | 03/010542 A1 | 2/2003 |
| WO | 2007074722 A1 | 7/2007 |
| WO | 2008006006 A1 | 1/2008 |
| WO | 2008008515 A2 | 1/2008 |

OTHER PUBLICATIONS

EPO, Office Action for the corresponding European patent application No. 11821768.6, dated Dec. 17, 2019.
Extended European Search Report dated Feb. 26, 2016; Application No./Patent No. 11821768.6—1554/2613138 PCT/JP2011069553; Applicant: Konica Minolta Medical & Graphic, Inc., et al.; Total of 8 pages.
Japanese language PCT International Preliminary Report on Patentability dated Mar. 12, 2013 and English translation.
Japanese Office Action dated Oct. 21, 2015 for corresponding Japanese Application No. 2012-531879 and English translation.
Ojima, et al.; Article HP-157-4, Jinsoku Keiko Men'eki HE Niju Senshokuho o Mochiita Atarashii Lymphsetsu Jinsoku Ten'l Shindanho; Journal of Japan Surgical Society, 2009, vol. 110; special extra issue 2, p. 660.
O. Katsumata, et al.; The Immunohistochemical Technique Using Semithin Cryosections; Dept. of Anatomy, Science Co; 1989, vol. 21; No. 10; pp. 398-402.
Pathology and Clinical Medicine; vol. 25, Extra Supplement, Immunohistochemistry useful for diagnosis, Bunkodo, 2007.

* cited by examiner

*Primary Examiner* — Tracy Vivlemore
*Assistant Examiner* — Nam P Nguyen
(74) *Attorney, Agent, or Firm* — Lucas & Mercanti, LLP (57) ABSTRACT

A biological substance detection method for detecting a biological substance specifically in a pathological specimen, includes a step of immunologically staining the pathological specimen using a fluorescent label, a step of staining the pathological specimen with a staining reagent for morphology observation purposes (eosin) to observe the morphology of the pathological specimen, a step of irradiating the stained pathological specimen with excited light to cause the emission of a fluorescent and detecting the biological substance in the pathological specimen. In the step of immunologically staining the pathological specimen, a special fluorescent particle for which the excitation wavelength appears in a region that is different from the excitation wavelength region of eosin is used as the fluorescent label.

18 Claims, 1 Drawing Sheet

BIOLOGICAL SUBSTANCE DETECTION METHOD

CROSS REFERENCE TO RELATED APPLICATION

This application is a continuation-in-part of U.S. patent application Ser. No. 13/819,453, filed on Feb. 27, 2013, which was a U.S. National Phase Application under 35 U.S.C. 371 of International Application PCT/JP2011/069553 filed on Aug. 30, 2011, which claimed the priority of Japanese Application No. 2010-193154 filed on Aug. 31, 2010, the entire content of these applications are hereby incorporated by reference.

TECHNICAL FIELD

The present invention relates to a biological substance detection method, and specifically relates to tissue staining for multiply staining a tissue with fluorescent labels.

BACKGROUND ART

As one of medical diagnoses, a pathological diagnosis is performed. A pathologist diagnoses a disease using a tissue section taken from a human body and notifies a clinician of the necessity or unnecessity of a therapy or operation. On the basis of conditions of a patient and pathological diagnosis, a physician determines a drug treatment plan, and a surgeon determines whether or not an operation should be performed.

In pathological diagnosis, it is widely performed to prepare a tissue sample by slicing a tissue specimen obtained through resection of an organ or needle biopsy into a thickness of about several micrometers and observe an enlarged image of the tissue sample with an optical microscope for obtaining various findings. In many cases, the sample is prepared by fixing a taken tissue through dehydration and paraffin blocking, slicing it into a thickness of several micrometers, and removing the paraffin. Since the sample, which barely absorbs and scatters light, is substantially colorless and transparent, staining with a dye is usually performed prior to the observation.

As a staining method, various staining methods have been proposed.

In particular for the tissue sample, hematoxylin-eosin staining (HE staining) using two dyes, hematoxylin and eosin, is typically used as a morphological observation staining for observing the morphology of the sample (Non-Patent Document 1 and Patent Documents 1 and 2).

The hematoxylin stains cell nuclei, calcareous sites, cartilage tissue, bacteria, and mucus to a color of from indigo blue to light blue. The eosin stains cytoplasm, interstitial tissue, various fibers, erythrocytes, and keratinocytes to a color of from red to deep red. A pathologist makes a diagnosis on the basis of morphological information and staining information such as changes in size and shape of cell nuclei and changes in tissue pattern in the microscopic image of the stained tissue sample.

As other staining for morphological observation, for example, Papanicolaou staining (Pap staining) used for cytodiagnosis is also known.

In pathological diagnosis, immunological observation called immunostaining where a molecular target is stained for confirming the expression of molecular information of a sample in order to diagnose dysfunction such as abnormal expression of a gene or a protein is performed.

The immunostaining, for example, employs dye staining with an enzyme (DAB staining). The DAB staining stains antigens as observation objects with antibodies modified so as to be stained by a dye, and measures the antigen level through observation. Alternatively, fluorescent labeling is employed. The fluorescent labeling stains antigens as objects with antibodies modified with a fluorescent dye and measures the antigen level through observation.

An attempt has currently been made to simultaneously perform morphological and immunological observations of a sample. For example, it has been tried to perform HE staining for morphological observation and DAB staining for immunological observation simultaneously (Patent Document 3).

However, the staining with an enzyme label such as DAB staining develops a color similar to the color in HE staining to preclude the distinction between the staining by an enzyme label and the HE staining, which makes the simultaneous observation difficult. In addition, in DAB staining, the concentration of the stain considerably varies depending on environmental conditions such as temperature and time to preclude the estimation of the actual amount of, for example, antibodies on the basis of the concentration of the stain.

Meanwhile, a fluorescent label is used in pathological diagnosis.

The fluorescence method has superior quantitative characteristics compared with DAB staining (Non-Patent Document 1).

However, simultaneous performance of pathological diagnosis and morphological observation with fluorescent labels has a disadvantage in that results of the staining are readily affected by the fluorescence of the staining reagent used for the tissue staining. A possible countermeasure is to use an infrared excitation/emission fluorescent dye which is not affected by visible light (Patent Document 4). For example, infrared-emitting dyes such as Alexa Fluor 647 (Molecular Probes) and CY5 (GE Healthcare) are known.

PRIOR ART DOCUMENTS

Patent Documents

[Patent Document 1] PCT Japanese Translation Patent Publication No. 2001-525580
[Patent Document 2] Japanese Patent Laid-Open No. 2009-115599
[Patent Document 3] Japanese Patent Laid-Open No. 2010-134195
[Patent Document 4] International Publication No. WO 2008/006006

Non-Patent Document

[Non-Patent Document 1] "Shindan ni yakudatsu men-eki soshiki shindan (Immunohistochemistry useful for diagnosis)", Bunkodo

SUMMARY OF THE INVENTION

Problem to be Solved by the Invention

Currently, a fluorescent dye is used in the immunofluorescent staining, which causes a problem that fluorescence intensity is low. In addition, in a case of using an infrared excitation/emission dye, an emission wavelength thereof is outside the visible light region. Thus, confirmation by visual observation is difficult, and an expensive detection device is required. Accordingly, the observation needs expensive instruments such as a confocal laser microscope.

Given the above, a main object of the present invention is to provide a method of detecting a biological substance, and the method is capable of discriminating between staining for morphological observation and immunostaining using fluorescent labels in simultaneous staining for morphological and immunological observation, without any infrared excitation/emission fluorescent dye.

Means for Solving the Problem

According to a first aspect of the present invention for solving the above-described problems, there is provided a biological substance detection method of specifically detecting a biological substance in a pathological section, and the biological substance detection method includes immunostaining the pathological section with a fluorescent label; staining the pathological section with a staining reagent for morphological observation; and detecting the biological substance in the pathological section through fluorescence emission by irradiation of the stained pathological section with excitation light, and in the immunostaining of the pathological section, a fluorescent nanoparticle including phosphor or a semiconductor and having an excitation wavelength region different from an excitation wavelength region of the staining reagent is used as the fluorescent label.

According to a second aspect of the present invention, there is provided a biological substance detection method of specifically detecting a biological substance in a pathological section, and the biological substance detection method includes immunostaining the pathological section with a fluorescent label; staining the pathological section with a staining reagent for morphological observation; and detecting the biological substance in the pathological section through fluorescence emission by irradiation of the stained pathological section with excitation light, and in the immunostaining of the pathological section, a fluorescent dye-containing particle including an organic or inorganic material particle containing a fluorescent dye and having an excitation wavelength region different from an excitation wavelength region of the staining reagent is used as the fluorescent label.

According to a third aspect of the present invention, there is provided a biological substance detection method of specifically detecting a biological substance in a pathological section, and the biological substance detection method includes immunostaining the pathological section with a fluorescent label, staining the pathological section with a staining reagent for morphological observation; and detecting the biological substance in the pathological section through fluorescence emission by irradiation of the stained pathological section with excitation light, and in the immunostaining of the pathological section, a fluorescent nanoparticle-containing particle including an organic or inorganic material particle containing a fluorescent nanoparticle including phosphor or a semiconductor and having an excitation wavelength region different from an excitation wavelength region of the staining reagent is used as the fluorescent label.

Effects of the Invention

According to the present invention, in simultaneous staining for morphological and immunological observation, the method can discriminate between staining for morphological observation and immunostaining using fluorescent labels, without any infrared excitation/emission fluorescent dye.

BEST MODE FOR CARRYING OUT THE INVENTION

Hereinafter, embodiments for implementing the present invention will be described. However, the present invention should not be limited thereto.

The method of detecting a biological substance according to a preferred embodiment of the present invention specifically detects a biological substance in a pathological section and basically includes step (1) of immunostaining the pathological section with a fluorescent label, step (2) of staining the pathological section with a staining reagent for morphological observation, and step (3) of detecting the biological substance in the pathological section through fluorescence emission by irradiation of the stained pathological section with excitation light.

In particular, in the step (1) of immunostaining the pathological section a specific fluorescent nanoparticle, a fluorescent dye-containing particle, or a fluorescent nanoparticle-containing particle having an excitation wavelength region different from the excitation wavelength region of the staining reagent for morphological observation is used as the fluorescent label.

The details of characteristics and types of the fluorescent label, the immunostaining, the staining for morphological observation and the like are as follows.

Here, either of the step (1) of immunostaining or the step (2) of staining for morphological observation may be performed first, that is, the order (former and latter) is not limited.

[Fluorescent Label]

Figure 1:
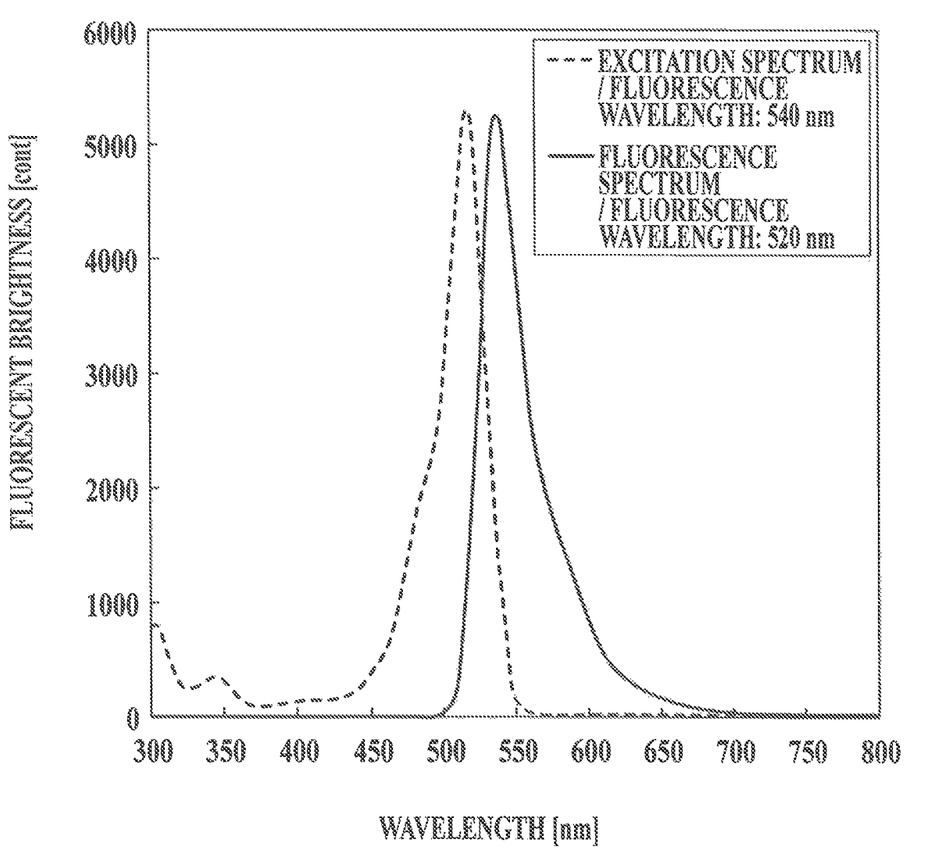
FIG. 1 This is a diagram schematically illustrating a fluorescence spectrum and an excitation spectrum of eosin.

Eosin used in HE staining emits fluorescence under certain conditions for microscopic observation. The absorption wavelength region of eosin overlaps the excitation wavelength regions of many fluorescent labels. Thus, there has been a problem that the light emission of eosin used for staining interferes with the observation of a fluorescent label. FIG. 1 shows a fluorescence spectrum (excitation wavelength: 520 nm) and an excitation spectrum (fluorescence wavelength: 540 nm) of eosin. The excitation spectrum shows that eosin is efficiently excited in a wavelength region of less than 350 nm and in a wavelength region of higher than 450 nm and less than 550 nm.

Thus, it is required that the fluorescent label according to the embodiment is excited in a wavelength region other than the above wavelength regions, i.e., in a wavelength region of 350 to 450 nm or in a longer wavelength region of 550 nm or more.

The emission wavelength of the fluorescent label according to the embodiment must be in the longer wavelength side of 550 nm or more in views of absorption and emission of eosin and tissue autofluorescence, and further, is preferably 700 nm or less in terms of necessity of visual confirmation in fluorescence microscopic observation. In particular, in terms of visual sensitivity, the emission wavelength of the fluorescent label according to the embodiment is preferably from 590 to 650 nm (590 nm or more and 650 nm or less) and more preferably from 590 to 630 nm (590 nm or more and 630 nm or less).

[Type of Fluorescent Label]

A fluorescent label having a higher brightness is preferred in terms of the signal ratio to the fluorescence of eosin and a cellular autofluorescence as noise. Thus, as the fluorescent label of the present invention, a fluorescent nanoparticle (A), a fluorescent dye-containing particle (B), or a fluorescent nanoparticle-containing particle (C) that has a high brightness level compared with brightness of a fluorescent dye is suitably used.

[(A) Fluorescent Nanoparticles]

The fluorescent nanoparticles used in the present invention have a particle size of 1 to 500 nm, preferably 10 to 200 nm.

The fluorescent nanoparticle is composed of a semiconductor or phosphor.

As for the semiconductor, a group II-VI semiconductor such as ZnSe, ZnTe, CdSe, CdTe, PbS, PbSe, PbTe, Cds, or ZnS, a group III-V semiconductor such as AlAs, AlSb, GaP, GaAs, GaSb, InP, InAs, InSb, InN, AlSe, or InGaP, Si, or Ge can be used. In terms of toxicity, GaP and InP are suitable used.

The phosphor can be an oxide phosphor. The phosphor is composed of, for example, a matrix of such as $Y_2O_3$, $YVO_4$, ZnO, or ZnS and an emission center of such as Eu or Nd.

The excitation wavelength can be adjusted to be suitable for observation by controlling the particle size, matrix composition, and impurity amount of the fluorescent nanoparticles. It is required that fluorescent nanoparticles are excited in the wavelength region of 350 to 450 nm or in a longer wavelength region of 550 nm or more, so as not to overlap the absorption wavelength region of eosin.

[(B) Fluorescent Dye-Containing Particles]

The fluorescent dye-containing particles used in the present invention are organic or inorganic particles containing a fluorescent dye.

The particles for containing a dye are made of, for example, polystyrene, polyamide, polylactic acid, polyacrylonitrile, polyglycidyl methacrylate, polymelamine, polyurea, polybenzoguanamine, polyfuran, polyxylene, a phenol resin, a polysaccharide, or silica that can stably contain phosphor. The dye may be introduced into the particles by any method. For example, the particles may be synthesized by binding dye molecules to a monomer as a raw material of the particles, or a dye may be introduced into particles by adsorption. The particle size ranges from 10 to 500 nm, and preferably from 50 to 200 nm.

It is required that the fluorescent dye to be contained can be excited in the wavelength region of 350 to 450 nm or in a longer wavelength region of 550 nm or more, so as not to overlap the absorption wavelength region of eosin.

As for the fluorescent dye to be contained, rhodamine dye molecules, Alexa Fluor (manufactured by Invitrogen Corporation) dye molecules, BODIPY (manufactured by Invitrogen Corporation) dye molecules, Texas Red dye molecules, squarylium dye molecules, cyanine dye molecules, oxazine dye molecules, aromatic ring dye molecules, and carbopyronine dye molecules can be given as examples.

Specific examples of the dye can be such as 5-carboxy-rhodamine, 6-carboxy-rhodamine, 5,6-dicarboxy-rhodamine, rhodamine 6G, tetramethylrhodamine, and X-rhodamine; Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, and BODIPY 650/665 (these are manufactured by Invitrogen Corporation); Cy5, Cy5.5, 1,3-bis[4-(dimethylamino)-2-hydroxyphenyl]-2,4-dihydroxycyclobutenediylium dihydroxide, bis(inner salt), 1,3-bis[4-(dimethylamino)phenyl]-2,4-dihydroxycyclobutenediylium dihydroxide, bis(inner salt), 2-(4-(diethylamino)-2-hydroxyphenyl)-4-(4-(diethyliminio)-2-hydroxycyclohexa-2,5-dienylidene)-3-oxocyclobut-1-enolate, 2-(4-(dibutylamino)-2-hydroxyphenyl)-4-(4-(dibutyliminio)-2-hydroxycyclohexa-2,5-dienylidene)-3-oxocyclobut-1-enolate, 2-(8-hydroxy-1,1,7,7-tetramethyl-1,2,3,5,6,7-hexahydropyrido[3,2,1-ij]quinolin-9-yl)-4-(8-hydroxy-1,1,7,7-tetramethyl-2,3,6,7-tetrahydro-1H-pyrido[3,2,1-ij]quinolinium-9(5H)-ylidene)-3-oxocyclobut-1-enolate, 1-butyl-2-[5-(1-butyl-1,3-dihydro-3,3-dimethyl-2H-indol-2-ylidene)-penta-1,3-dienyl]-3,3-dimethyl-3H-indolium hexafluorophosphate, 1-butyl-2-[5-(1-butyl-3,3-dimethyl-1,3-dihydro-indol-2-ylidene)-3-chloro-penta-1,3-dienyl]-3,3-dimethyl-3H-indolium hexafluorophosphate, 3-ethyl-2-[5-(3-ethyl-3H-benzothiazol-2-ylidene)-penta-1,3-dienyl]-benzothiazol-3-ium iodide, N,N-di-(2,6-diisopropylphenyl)-1,6,7,12-(4-tert-butyl-phenoxy)-perylen-3,4,9,10-tetracarbonic acid diimide, N,N-bis(2,6-diisopropylphenyl)-1,6,7,12-tetraphenoxyperylene-3,4:9,10-tetracarboxdiimide, N,N'-bis(2,6-diisopropylphenyl)perylene-3,4:9,10-bis(dicarbimide), benzenesulfonic acid, 4,4',4'',4'''-[[2,9-bis[2,6-bis(1-methylethyl)phenyl]-1,2,3,8,9,10-hexahydro-1,3,8,10-tetraoxoanthra[2,1,9-def:6,5,10-d'e'f']diisoquinoline-5,6,12,13-tetrayl]tetrakis(oxy)]tetrakis-, benzeneethanaminium, 4,4',4'',4'''-[[2,9-bis[2,6-bis(1-methylethyl)phenyl]-1,2,3,8,9,10-hexahydro-1,3,8,10-tetraoxoanthra[2,1,9-def:6,5,10-d'e'f']diisoquinoline-5,6,12,13-tetrayl]tetrakis(oxy)]tetrakis[N,N,N-trimethyl-, ROX (X-Rhodamine, Rhodamine Red X), DY-590, 5-ROX, Spectrum Red, PYRROMETHENE 650, Texas Red, BODIPY TR, DyLight 594, AlexaFluor 594, HiLyte 594, HiLyte Fluor TR, Cresyl violet, ATTO 590, MFP 590, DY-610, ATTO 610, DY-615, Oxazine 170, ATTO 620, C-phycocyanin, Alexa Fluor 633, phycocyanin, ATTO 633, DY-630, DY-632, DY-633, MFP 631, DyLight 633, Northern Lights 637, DY-631, DY-634, Nile Blue, Allophycocyanin (APC), APC-XL, EVOblue 30, SRFluor 680-Carboxylate, LD 700 Perchlorate, and ATTO 655. These fluorescent dyes may be used alone or as a mixture thereof.

[(C) Fluorescent Nanoparticle-Containing Particles]

The fluorescent nanoparticle-containing particles used in the present invention are organic or inorganic particles containing the fluorescent nanoparticles described in the above (A).

The fluorescent nanoparticles may be introduced into the particles by any method. For example, the particles may be synthesized by binding fluorescent nanoparticles to a monomer as a raw material of the particles, or fluorescent nanoparticles may be introduced into particles by adsorption.

The excitation wavelength can be adjusted to be suitable for observation by controlling the particle size, matrix composition, and impurity level of the fluorescent nanoparticles to be contained.

It is required that the fluorescent nanoparticles are excited in the wavelength region of 350 to 450 nm or in a longer wavelength region of 550 nm or more, so as not to overlap the absorption wavelength region of eosin. The types of phosphor described in the above section regarding the fluorescent nanoparticles are given as examples.

The size of the particles containing the fluorescent nanoparticles ranges from 10 to 500 nm, and preferably from 50 to 200 nm.

[Staining for Morphological Observation]

In the staining for morphological observation, particularly regarding the staining for morphological observation of tissue samples, hematoxylin-eosin staining (HE staining) using two dyes, hematoxylin and eosin, is typically used in the staining for morphological observation of the morphology of a sample. The staining for morphological observation is not limited thereto, and examples of other staining for morphological observation is such as Papanicolaou staining (Pap staining) used for cytodiagnosis.

In the HE staining, the hematoxylin stains cell nuclei, calcareous sites, cartilage tissue, bacteria, and mucus to a color of from indigo blue to light blue; and the eosin stains cytoplasm, interstitial tissue, various fibers, erythrocytes, and keratinocytes to a color of from red to deep red. However, the staining for morphological observation is not limited thereto. Cell nuclei, calcareous sites, cartilage tissue, bacteria, and mucus may be stained by a hematoxylin analog or a dye having an absorption wavelength similar to an absorption wavelength of hematoxylin to a color of from indigo blue to light blue; and cytoplasm, interstitial tissue, various fibers, erythrocytes, and keratinocytes may be stained by an eosin analog or a dye having an absorption wavelength similar to an absorption wavelength of eosin to a color of from red to deep red.

[Immunostaining]

As a method of immunostaining of a tissue, fluorescent staining is suitable used.

The fluorescent staining is a method of staining an antigen site with a fluorescent label. As a method other than the fluorescent staining, for example, dye staining with an enzyme (DAB staining) is known. However, this method is inferior to the fluorescent staining in sensitivity.

Staining can be performed by, for example, a method of staining an antigen with a label prepared by directly binding a fluorescent label to primary antibodies (primary antibody method); a method of staining an antigen to which a primary antibody is bound with a label prepared by directly binding a fluorescent label to secondary antibodies (secondary antibody method); or a method of staining an antigen to which primary antibodies are bound and secondary antibodies modified by avidin or streptavidin with a label prepared by directly binding a fluorescent label to biotin (biotin-avidin method or sandwich method).

A Primary antibody used in staining may be any antibody and is selected depending on the target to be subjected to immunostaining of a tissue. For example, staining of an HER2 antigen uses an anti-HER2 antibody. A secondary antibody may be any antibody and is selected depending on the primary antibody. For example, anti-mouse, rabbit, bovine, goat, sheep, dog, and chicken antibodies can be given as examples.

The fluorescent label may be bound to an antibody or biotin by any known method, for example, amidation of carboxylic acid with amide, sulfidation of maleimide with thiol, imination of aldehyde with amine, or amination of epoxy with amine.

Although tissue staining has been described above, the present invention is not limited thereto and can also be applied to cell staining.

EXAMPLES

Hereinafter, the present invention will be described in detail by Examples, but is not limited thereto.

[Preparation of Samples]

(Sample 1: Fluorescent Nanoparticles)

CdSe/ZnS fluorescent nanoparticles (Qdot655, Invitrogen Corporation) modified with PEG having amino groups at the ends were prepared as fluorescent nanoparticles for antibody binding.

Meanwhile, anti-human ER antibodies were subjected to reduction treatment with 1M dithiothreitol (DTT), and excess DTT was removed by a gel filtration column to obtain a solution of the reduced antibodies capable of bonding to silica particles.

The fluorescent nanoparticles for antibody binding and the reduced antibodies were mixed in PBS containing 2 mM EDTA, followed by reaction for 1 hour. The reaction was stopped by adding 10 mM mercaptoethanol. The obtained solution was concentrated with a centrifugal filter, and subsequently, the unreacted antibodies and the like were removed by a gel filtration column for purification to obtain fluorescent nanoparticles to which the anti-human ER antibodies were bound.

(Sample 2: Fluorescent Nanoparticles)

The same fluorescent nanoparticles to which the anti-human ER antibodies were bound as sample 1 were prepared.

In the observation described below, sample 1 was observed at an excitation wavelength of 375 nm, and sample 2 was observed at an excitation wavelength of 575 nm. That is, the same fluorescent nanoparticles prepared as samples 1 and 2 were observed at different excitation wavelengths.

(Sample 3: Fluorescent Nanoparticles)

CdSe/ZnS fluorescent nanoparticles (Qdot605, Invitrogen Corporation) modified with PEG having amino groups at the ends were used as fluorescent nanoparticles for antibody binding.

Fluorescent nanoparticles to which the anti-human ER antibodies were bound were prepared as sample 1 with the exception described above.

(Sample 4: Fluorescent Dye-Containing Particles)

An organoalkoxysilane compound was obtained by mixing 9.9 mg of the fluorescent dye, CY5-SE (manufactured by Roche) and 3 μL of 3-aminopropyltrimethoxysilane (KBM903, manufactured by Shin-Etsu Silicone) in DMF. The obtained organoalkoxysilane compound in an amount of 0.6 mL was mixed with 48 mL of ethanol, 0.6 mL of tetraethoxysilane (TEOS), 2 mL of water, and 2 mL of 28% aqueous ammonia for 3 hours. The liquid mixture prepared in the above was centrifuged at 10000 G for 20 minutes, and the supernatant was removed. Thereafter, ethanol was added to disperse the precipitate therein, and the solution was centrifuged again. The precipitate was washed twice with each of ethanol and pure water by the same procedure. The obtained tetramethylrhodamine-containing silica nanoparticles were observed with an SEM. The average particle diameter was 104 nm, and the coefficient of variation was 12%.

The obtained phosphor-containing silica nanoparticles were adjusted to a 3 nM concentration with a phosphate buffer physiological saline solution (PBS) containing 2 mM ethylenediaminetetraacetic acid (EDTA). This solution was mixed with SM(PEG)12 (succinimidyl-[(N-maleimidopropionamido)-dodecaethyleneglycol] ester, manufactured by Thermo Scientific K.K.) in a final concentration of 10 mM, followed by reaction for 1 hour. The solution mixture was centrifuged at 10000 G for 20 minutes. The supernatant was removed. Thereafter, PBS containing 2 mM EDTA was added to disperse the precipitate therein. The solution was centrifuged again. The precipitate was washed three times by the same procedure to obtain fluorescent dye-containing particles for antibody binding.

Meanwhile, anti-human ER antibodies were subjected to reduction treatment with 1M dithiothreitol (DTT), and excess DTT was removed by a gel filtration column to obtain a solution of the reduced antibodies capable of bonding to silica particles.

The fluorescent dye-containing particles for antibody binding and the reduced antibodies prepared above were mixed in PBS containing 2 mM EDTA, followed by reaction for 1 hour. The reaction was stopped by adding 10 mM mercaptoethanol. The obtained solution was centrifuged at 10000 G for 20 minutes, and the supernatant was removed. Thereafter, PBS containing 2 mM EDTA was added to disperse the precipitate therein. The solution was centrifuged again. The precipitate was washed three times by the same procedure to obtain fluorescent dye-containing particles to which the anti-human ER antibodies were bound.

(Sample 5-1: Fluorescent Dye-Containing Particles)

TAMRA dye (manufactured by PCC) was used as a fluorescent dye.

Fluorescent dye-containing particles to which the anti-human antibodies were bound were synthesized as sample 4 with the exception described above.

(Sample 5-2: Fluorescent Dye-Containing Particles)

Texas Red dye (manufactured by Sigma-Aldrich Co.) was used as a fluorescent dye.

Fluorescent dye-containing particles to which the anti-human antibodies were bound were synthesized as sample 4 with the exception described above.

(Sample 5-3: Fluorescent Dye-Containing Particles)

Oxazine 170 dye (manufactured by Sigma-Aldrich Co.) was used instead of the fluorescent dye in the preparation of sample 4, and 3-glycidyloxypropyltrimethoxysilane (manufactured by TCI CO., LTD.) was used instead of 3-aminopropyltrimetoxysilane (KBM903, manufactured by Shin-Etsu Silicone).

Fluorescent dye-containing particles to which the anti-human antibodies were bound were synthesized as sample 4 with the exceptions described above.

(Sample 5-4: Fluorescent Dye-Containing Particles)

First, 2.5 mg of Oxazine 170 (manufactured by Sigma-Aldrich Co.) was added to 22.5 mL of water, and subsequently placed on a hot stirrer and was heated at 60° C. for 20 minutes. Then, 1.5 g of Nikalac MX-035 (manufactured by Nippon Carbide Industries Co., Inc.) was added thereto, followed by heating with stirring for further 5 minutes.

Subsequently, 100 µL of formic acid was added to the above solution, followed by heating with stirring at 60° C. for 20 minutes, and then the solution was cooled at room temperature.

After cooling, the reaction mixture was put in a centrifuge tube, and the tube was set to a centrifugal separator, followed by centrifugation at 12000 rpm for 20 minutes. The supernatant was removed.

Subsequently, the reaction mixture after the supernatant was removed was washed with ethanol and water.

The obtained particles were modified with anti-human ER antibodies using SM(PEG)12 (succinimidyl-[(N-maleimidopropionamido)-dodecaethyleneglycol] ester, manufactured by Thermo Scientific K.K.) as sample 4 to obtain fluorescent dye-containing particles for antibody binding.

Fluorescent dye-containing particles to which the anti-human antibodies were bound were synthesized as sample 4 with the exceptions described above.

(Sample 5-5: Fluorescent Dye-Containing Particles)

Texas Red dye (manufactured by Sigma-Aldrich Co.) was used as a fluorescent dye.

A phenol resin was used for the particles for containing the dye.

Fluorescent dye-containing particles to which the anti-human antibodies were bound were synthesized as sample 4 with the exceptions described above.

(Sample 5-6: Fluorescent Dye-Containing Particles)

Texas Red dye (manufactured by Sigma-Aldrich Co.) was used as a fluorescent dye.

Polyfuran was used for the particles for containing the dye.

Fluorescent dye-containing particles to which the anti-human antibodies were bound were synthesized as sample 4 with the exceptions described above.

(Sample 5-7: Fluorescent Dye-Containing Particles)

Texas Red dye (manufactured by Sigma-Aldrich Co.) was used as a fluorescent dye.

A PS/GMA complex was used for the particles for containing the dye.

Fluorescent dye-containing particles to which the anti-human antibodies were bound were synthesized as sample 4 with the exceptions described above.

(Sample 5-8: Fluorescent Dye-Containing Particles)

Texas Red dye (manufactured by Sigma-Aldrich Co.) was used as a fluorescent dye.

A PS/PMMA complex was used for the particles for containing the dye.

Fluorescent dye-containing particles to which the anti-human antibodies were bound were synthesized as sample 4 with the exceptions described above.

(Sample 5-9: Fluorescent Dye-Containing Particles)

Texas Red dye (manufactured by Sigma-Aldrich Co.) was used as a fluorescent dye.

A PS/acrylonitrile complex was used for the particles for containing the dye.

Fluorescent dye-containing particles to which the anti-human antibodies were bound were synthesized as sample 4 with the exceptions described above.

(Sample 5-10: Fluorescent Dye-Containing Particles)

Texas Red dye (manufactured by Sigma-Aldrich Co.) was used as a fluorescent dye.

A PS/acetonitrile/GMA complex was used for the particles for containing the dye.

Fluorescent dye-containing particles to which the anti-human antibodies were bound were synthesized as sample 4 with the exceptions described above.

(Sample 6: Fluorescent Nanoparticle-Containing Particles)

As fluorescent nanoparticles, 10 µL of a CdSe/ZnS decane dispersion (Qdot655, Invitrogen Corporation) was provided, and the dispersion was mixed with 40 µL of tetraethoxysilane. Meanwhile, 4 mL of ethanol and 1 mL of 14% aqueous ammonia were mixed, followed by stirring at room temperature. To this mixture, the above mixture of the CdSe/ZnS decane dispersion and tetraethoxysilane prepared above was added, followed by stirring for 12 hours after the addition to obtain fluorescent nanoparticle-containing particles. The reaction solution was centrifuged at 10000 G for 30 minutes, and the supernatant was removed. Thereafter, ethanol was added to disperse the precipitate therein, and the solution was centrifuged again for washing the fluorescent nanoparticle-containing particles. The particles were washed once with each of ethanol and pure water by the same procedure. The obtained fluorescent nanoparticle-containing particles were observed with an SEM. The average particle diameter was 120 nm, and the coefficient was variation of 12%.

The obtained fluorescent nanoparticle-containing particles were adjusted to a 3 nM concentration with a phosphate buffer physiological saline solution (PBS) containing 2 mM ethylenediaminetetraacetic acid (EDTA). This solution was mixed with SM(PEG)12 (succinimidyl-[(N-maleimidopropionamido)-dodecaethyleneglycol] ester, manufactured by Thermo Scientific K.K.) in a final concentration of 10 mM, followed by reaction for 1 hour. The mixture was centrifuged at 10000 G for 20 minutes. The supernatant was removed, and the precipitate was dispersed in PBS containing 2 mM EDTA. The solution was centrifuged again. The precipitate was washed three times by the same procedure to obtain fluorescent nanoparticle-containing particles for antibody binding.

Meanwhile, anti-human ER antibodies were subjected to reduction treatment with 1M dithiothreitol (DTT), and excess DTT was removed by a gel filtration column to obtain a solution of the reduced antibodies capable of bonding to fluorescent nanoparticle-containing particles.

The fluorescent nanoparticle-containing particles for antibody binding and the reduced antibodies prepared above were mixed in PBS containing 2 mM EDTA, followed by reaction for 1 hour. The reaction was stopped by adding 10 mM mercaptoethanol to the reaction system. The obtained solution was centrifuged at 10000 G for 20 minutes, and the supernatant was removed. Thereafter, PBS containing 2 mM EDTA was added to disperse the precipitate therein. The solution was centrifuged again. The precipitate was washed three times by the same procedure to obtain fluorescent nanoparticle-containing particles to which the anti-human ER antibodies were bound.

(Sample 7: Fluorescent Nanoparticle-Containing Particles)

The same fluorescent nanoparticle-containing particles to which the anti-human ER antibodies were bound as sample 6 were prepared.

In the observation described below, sample 6 was observed at an excitation wavelength of 375 nm, and sample 7 was observed at an excitation wavelength of 575 nm. That is, the same fluorescent nanoparticles prepared as samples 6 and 7 were observed at different excitation wavelengths.

(Sample 8: Fluorescent Nanoparticle-Containing Particles)

A CdSe/ZnS decane dispersion (Qdot605, Invitrogen Corporation) was used as fluorescent nanoparticles.

Fluorescent nanoparticle-containing particles to which the anti-human antibodies were bound were prepared as sample 6 with the exception described above.

(Sample 9: Fluorescent Nanoparticle-Containing Particles)

A CdSe/ZnS decane dispersion (Qdot705, Invitrogen Corporation) was used as fluorescent nanoparticles.

Fluorescent nanoparticle-containing particles to which the anti-human ER antibodies were bound were prepared as sample 6 with the exception described above.

(Sample 11: Fluorescent Dye)

A fluorescent dye was prepared by binding CY5 dye (manufactured by Invitrogen Corporation) to anti-human ER antibodies as sample 1.

(Sample 12: Fluorescent Dye)

A fluorescent dye was prepared by binding TAMRA dye (manufactured by PCC) to anti-human ER antibodies by the same way as sample 1.

(Sample 13: Fluorescent Dye)

A fluorescent dye was prepared by binding FITC dye (manufactured by PCC) to anti-human ER antibodies by the same way as sample 1.

(Sample 14: Fluorescent Nanoparticles)

The same fluorescent nanoparticles to which the anti-human ER antibodies were bound as sample 1 were prepared.

Sample 14 was excited at an excitation wavelength of 300 nm in the observation described below.

(Sample 15: Fluorescent Nanoparticles)

The same fluorescent nanoparticles to which the anti-human ER antibodies were bound as sample 1 were prepared.

Sample 15 was excited at an excitation wavelength of 500 nm in the observation described below.

(Sample 16: Fluorescent Nanoparticles)

CdSe/ZnS fluorescent nanoparticles (Qdot565, Invitrogen Corporation) modified with PEG having amino groups at the ends were used as fluorescent nanoparticles for antibody binding.

Fluorescent nanoparticles to which the anti-human ER antibodies were bound were prepared as sample 1 with the exception described above.

(Sample 17: Fluorescent Dye-Containing Particles)

FITC dye (manufactured by PCC) was used as a fluorescent dye.

Fluorescent dye-containing particles to which the anti-human ER antibodies were bound were synthesized as sample 4 with the exception described above.

(Sample 18: Fluorescent Nanoparticle-Containing Particles)

The same fluorescent nanoparticle-containing particles to which the anti-human ER antibodies were bound as sample 6 were prepared.

Sample 18 was excited at an excitation wavelength of 300 nm in the observation described below.

(Sample 19: Fluorescent Nanoparticle-Containing Particles)

The same fluorescent nanoparticle-containing particles to which the anti-human ER antibodies were bound as sample 6 were prepared.

Sample 19 was excited at an excitation wavelength of 500 nm in the observation described below.

(Sample 20: Fluorescent Nanoparticle-Containing Particles)

A CdSe/ZnS decane dispersion (Qdot565, Invitrogen Corporation) was used as fluorescent nanoparticles.

Fluorescent nanoparticle-containing particles to which the anti-human ER antibodies were bound were prepared as sample 6 with the exception described above.

[Evaluation by Tissue Staining]

Human mammary tissue was subjected to immunostaining and staining for morphological observation (HE staining) with samples 1 to 9 and 11 to 20.

A tissue array slide (CB-A712) manufactured by Cosmo Bio Co., Ltd was used as a section to be stained. The tissue array slide was deparaffinized and then subjected to displacement washing with water and autoclave treatment in a 10 mM citrate buffer solution (pH 6.0) for 15 minutes to activate the antigen. The tissue array slide after the activation treatment of the antigen was washed with a PBS buffer solution and was subjected to blocking treatment with a PBS buffer solution containing 1% BSA in a moist chamber for 1 hour. After the blocking treatment, each of samples 1 to 9 and 11 to 20 diluted with a PBS buffer solution containing 1% BSA to a 0.05 nM concentration was reacted with the tissue section for 3 hours. After the reaction with each of sample 1 to 9 and 11 to 20, the tissue array slide was washed with a PBS buffer solution.

After the immunostaining, staining for morphological observation (HE staining) was performed.

The immunostained section was stained with hematoxylin by Mayer's hematoxylin solution for 5 minutes, and then washed with running water (about 45° C.) for 3 minutes. Subsequently, the section was stained with eosin by a 1% eosin solution for 5 minutes and was immersed in pure ethanol for 5 minutes. The immersion in pure ethanol was repeated four times for washing and dehydration. Subsequently, the section was immersed in xylene for 5 minutes four times for clearing. Finally, sealing with a sealing agent, Entellan New (manufactured by Merck KGaA), was performed to obtain a sample slide for observation.

The tissue sections which were immunostained with samples 1 to 9 and 11 to 20 and subjected to staining for morphological observation were irradiated with excitation light to emit fluorescence, and images from the tissue sections were obtained with an inverted fluorescence microscope (manufactured by Carl Zeiss).

The excitation wavelength (nm) and the fluorescence wavelength (nm) were set with an optical filter (the excitation wavelengths and the fluorescence wavelengths of optical filters shown in Tables 1 to 4 are central values). The exposure conditions for obtaining microscopic images at each excitation wavelength were adjusted so that the total irradiation energy approximately at the focal point was 50 J.

The brightness of each pixel was calculated from the obtained image with Image-J, and the average brightness (labeled site brightness) of the sites stained with the fluorescent label (labeled site) was calculated. The average brightness corresponds to a signal value (S). A brightness of "0" is black (most dark), and a brightness of "255" is white (most bright). In addition, the average brightness (eosin-stained site brightness) of the sites that were not labeled with the fluorescent dye, but stained with eosin in the area near the fluorescent labeled cells (eosin-stained site) was calculated. The average brightness corresponds to a noise value (N).

A ratio of the labeled site brightness to the eosin-stained site brightness was determined as an S/N ratio. An S/N ratio of 1.5 or more provided easy discrimination of a labeled site from an eosin-stained site. Accordingly, the S/N ratio of 1.5 was determined as a criterion value.

Fluorescence was also visually observed during the obtainment of microscopic images to evaluate the availability of visual observation.

In Tables 1 to 4, "Experimental Examples 1 to 9 and 11 to 20" corresponding to the evaluation experiments with samples 1 to 9 and 11 to 20 are shown. Tables 1 to 4 show the type of fluorescent label, the excitation wavelength, the fluorescence wavelength, the labeled site brightness, the eosin-stained site brightness, the S/N ratio, the discriminateness (S/N ratio evaluation), the color visibility of the fluorescent label (visual observability) of each of Experimental Examples 1 to 9 and 11 to 20.

At the S/N ratio of 1.5 or more, a labeled site can be easily discriminated from an eosin-stained site. Accordingly, as for the discriminateness (S/N ratio evaluation), a ratio of 1.5 or more is determined to be "○ (suitable)", and a ratio of less than 1.5 is determined to be "X (unsuitable)".

As for the color visibility of the fluorescent label (visual observability), a fluorescent label that was easily recognized by visual observation was determined to be "○", a fluorescent label that was difficult to be recognized is determined to be "Δ", and a fluorescent label that was not recognized at all is determined to be "X".

TABLE 1

|  | EXPERIMENTAL EXAMPLE | | | |
| --- | --- | --- | --- | --- |
|  | 1 (Example) | 2 (Example) | 3 (Example) | 4 (Example) |
| Sample | 1 | 2 | 3 | 4 |
| Fluorescent label | Fluorescent nanoparticle | | | Fluorescent dye-containing particle |
| Excitation wavelength (nm) | 375 | 575 | 575 | 600 |
| Fluorescence wavelength (nm) | 640 | 640 | 605 | 640 |
| Brightness of labeled site | 21.0 | 10.5 | 10.5 | 105.0 |
| Brightness of eosin-stained site | 14.0 | 7.0 | 7.2 | 5.6 |
| S/N ratio | 1.5 | 1.5 | 1.5 | 18.8 |
| Discriminateness (S/N ratio evaluation) | ○ | ○ | ○ | ○ |
| Color visibility of fluorescent label | Δ | Δ | ○ | Δ |

TABLE 2

|  | EXPERIMENTAL EXAMPLE | | | | |
| --- | --- | --- | --- | --- | --- |
|  | 5-1 (Example) | 5-2 (Example) | 5-3 (Example) | 5-4 (Example) | 5-5 (Example) |
| Sample | 5-1 | 5-2 | 5-3 | 5-4 | 5-5 |
| Fluorescent label | Fluorescent dye-containing particle | | | | |
| Excitation wavelength (nm) | 550 | 585 | 600 | 600 | 585 |
| Fluorescence wavelength (nm) | 575 | 620 | 640 | 640 | 620 |
| Brightness of labeled site | 105.0 | 150.0 | 25.0 | 75.0 | 105.0 |
| Brightness of eosin-stained site | 10.5 | 10.5 | 10.5 | 10.5 | 10.5 |
| S/N ratio | 10.0 | 14.3 | 2.4 | 7.1 | 10.0 |
| Discriminateness (S/N ratio evaluation) | ○ | ○ | ○ | ○ | ○ |
| Color visibility of fluorescent label | ○ | ○ | Δ | Δ | ○ |

TABLE 2-continued

| | EXPERIMENTAL EXAMPLE | | | | |
|---|---|---|---|---|---|
| | 5-6 (Example) | 5-7 (Example) | 5-8 (Example) | 5-9 (Example) | 5-10 (Example) |
| Sample | 5-6 | 5-7 | 5-8 | 5-9 | 5-10 |
| Fluorescent label | Fluorescent dye-containing particle | | | | |
| Excitation wavelength (nm) | 585 | 585 | 585 | 585 | 585 |
| Fluorescence wavelength (nm) | 620 | 620 | 620 | 620 | 620 |
| Brightness of labeled site | 90.0 | 85.0 | 102.0 | 110.0 | 80.0 |
| Brightness of eosin-stained site | 10.5 | 10.5 | 10.5 | 10.5 | 10.5 |
| S/N ratio | 8.6 | 8.1 | 9.7 | 10.5 | 7.6 |
| Discriminateness (S/N ratio evaluation) | ○ | ○ | ○ | ○ | ○ |
| Color visibility of fluorescent label | ○ | ○ | ○ | ○ | ○ |

TABLE 3

| | EXPERIMENTAL EXAMPLE | | | |
|---|---|---|---|---|
| | 6 (Example) | 7 (Example) | 8 (Example) | 9 (Example) |
| Sample | 6 | 7 | 8 | 9 |
| Fluorescent label | Fluorescent nanoparticle-containing particle | | | |
| Excitation wavelength (nm) | 375 | 575 | 575 | 375 |
| Fluorescence wavelength (nm) | 640 | 640 | 605 | 720 |
| Brightness of labeled site | 210.0 | 105.0 | 105.0 | 84 |
| Brightness of eosin-stained site | 14.0 | 7.0 | 7.2 | 5.6 |
| S/N ratio | 15.0 | 15.0 | 14.6 | 15 |
| Discriminateness (S/N ratio evaluation) | ○ | ○ | ○ | ○ |
| Color visibility of fluorescent label | ○ | ○ | ○ | X |

TABLE 4

| EXPERIMENTAL EXAMPLE | 11 (Comparative Example) | 12 (Comparative Example) | 13 (Comparative Example) | 14 (Comparative Example) | 15 (Comparative Example) | 16 (Comparative Example) |
|---|---|---|---|---|---|---|
| Sample | 11 | 12 | 13 | 14 | 15 | 16 |
| Fluorescent label | Fluorescent dye alone | | | Fluorescent nanoparticle | | |
| Excitation wavelength (nm) | 600 | 550 | 470 | 300 | 500 | 475 |
| Fluorescence wavelength (nm) | 640 | 575 | 500 | 640 | 640 | 565 |
| Brightness of labeled site | 5.7 | 10.6 | 35.7 | 15.4 | 14.7 | 24.5 |
| Brightness of eosin-stained site | 5.6 | 10.5 | 35.0 | 14.0 | 13.3 | 21.0 |
| S/N ratio | 1.0 | 1.0 | 1.0 | 1.1 | 1.1 | 1.2 |
| Discriminateness (S/N ratio evaluation) | x | x | x | x | x | x |
| Color visibility of fluorescent label | Δ | ○ | ○ | Δ | Δ | ○ |

| EXPERIMENTAL EXAMPLE | 17 (Comparative Example) | 18 (Comparative Example) | 19 (Comparative Example) | 20 (Comparative Example) |
|---|---|---|---|---|
| Sample | 17 | 18 | 19 | 20 |
| Fluorescent label | Fluorescent dye-containing particle | Fluorescent nanoparticle-containing particle | | |
| Excitation wavelength (nm) | 470 | 300 | 500 | 475 |
| Fluorescence wavelength (nm) | 500 | 640 | 640 | 565 |
| Brightness of labeled site | 36.4 | 123.2 | 117.6 | 171.5 |
| Brightness of eosin-stained site | 35.0 | 98.0 | 93.1 | 136.5 |

TABLE 4-continued

| | | | | |
|---|---|---|---|---|
| S/N ratio | 1.0 | 1.3 | 1.3 | 1.3 |
| Discriminateness (S/N ratio evaluation) | x | x | x | x |
| Color visibility of fluorescent label | ○ | Δ | Δ | ○ |

As shown in Tables 1 to 4, Experimental Examples 1 to 9 and 11 to 13 compare the cases of using fluorescent nanoparticles, fluorescent dye-containing particles, or fluorescent nanoparticles-containing particles with the cases of using fluorescent dye alone. In the cases of using fluorescent nanoparticles, fluorescent dye-containing particles, and fluorescent nanoparticles-containing particles, the difference in brightness between the labeled sites and the eosin-stained sites was larger, and the S/N ratios of the fluorescent labels were higher, compared to the cases of the fluorescent dye alone. In the cases of using the fluorescent dye alone, S/N ratios were low so that visual observation of the labeled sites was impossible.

Experimental Examples 1 to 3 and 14 to 16 compare the cases of exciting fluorescent nanoparticles at the excitation wavelengths different from that of eosin (Experimental Examples 1 to 3) with the cases of exciting at excitation wavelengths coinciding with the excitation wavelength of eosin (Experimental Examples 14 to 16). The S/N ratios were higher when the excitation wavelengths were different from the excitation wavelength of eosin than the S/N ratios when the excitation wavelengths coincided with the excitation wavelength of eosin. Similar relationships are also obtained in Experimental Examples 4, 5, and 17 using fluorescent dye-containing particles and Experimental Examples 6 to 9 and 18 to 20 using fluorescent nanoparticles-containing particles.

As described above, a high S/N ratio and discrimination between immunostaining and staining for morphological observation can be achieved in the case of using a fluorescent label of specific fluorescent nanoparticles, fluorescent dye-containing particles, or fluorescent nanoparticles-containing particles having an excitation wavelength in a wavelength region (a wavelength region of 350 to 450 nm or a longer wavelength region of 550 nm or more) other than the excitation wavelength regions (a range of less than 350 nm and a range of higher than 450 nm and less than 550 nm) of eosin.

Experimental Examples 7 to 9 compare the emission color visibilities of the fluorescent label at different fluorescence wavelengths. In Experimental Example 9, the emission wavelength (fluorescence wavelength) was close to the near-infrared region, and the labeled site was therefore difficult to be recognized by visual observation. In order to confirm a labeled site by visual observation, the fluorescent label preferably has an emission wavelength of 550 to 700 nm.

INDUSTRIAL APPLICABILITY

The present invention can be used for specifically detecting a biological substance in a pathological section when staining for morphological observation and immunostaining are simultaneously performed.

What is claimed is:

1. A method of specifically detecting a substance to be detected in a pathological section, the method comprising:
immunostaining the pathological section with a fluorescent label;
staining the pathological section with a staining reagent;
observing morphology of the pathological section; and
detecting the substance to be detected in the pathological section by irradiating the stained pathological section with excitation light and detecting fluorescence emitted therefrom, wherein
the fluorescent label has an excitation wavelength region different from an excitation wavelength region of the staining reagent, and
the stained pathological section is not irradiated with excitation light having the excitation wavelength region of the staining reagent.

2. A method of specifically detecting a substance to be detected in a pathological section, the method comprising:
immunostaining the pathological section with a fluorescent label;
staining the pathological section with a staining reagent;
observing morphology of the pathological section; and
detecting the substance to be detected in the pathological section by irradiating the stained pathological section with excitation light and detecting fluorescence emitted therefrom, wherein
in the immunostaining of the pathological section, a fluorescent nanoparticle-containing particle comprising an organic or inorganic material particle containing a fluorescent nanoparticle comprising phosphor or a semiconductor and having an excitation wavelength region different from an excitation wavelength region of the staining reagent is used as the fluorescent label, and
the stained pathological section is not irradiated with excitation light having the excitation wavelength region of the staining reagent.

3. The method according to claim 1, wherein
the fluorescent label has an excitation wavelength in a wavelength region of 350 to 450 nm or in a longer wavelength region of 550 nm or more; and
the staining reagent is eosin having excitation wavelengths in a region of less than 350 nm and a wavelength region of higher than 450 nm and less than 550 nm.

4. The method according to claim 3, wherein
the fluorescent label has an emission wavelength in a wavelength region of 550 to 700 nm.

5. The method according to claim 3, wherein
the fluorescent label has an emission wavelength in a wavelength region of 590 to 650 nm.

6. The method according to claim 3, wherein
the fluorescent label has an emission wavelength in a wavelength region of 590 to 630 nm.

7. The method according to claim 2, wherein
the fluorescent nanoparticle of the fluorescent nanoparticle-containing particle is composed of a semiconductor or an oxide phosphor.

8. The method according to claim 2, wherein
the fluorescent label has an excitation wavelength in a wavelength region of 350 to 450 nm or in a longer wavelength region of 550 nm or more; and
the staining reagent is eosin having excitation wavelengths in a region of less than 350 nm and a wavelength region of higher than 450 nm and less than 550 nm.

9. The method according to claim 8, wherein
the fluorescent label has an emission wavelength in a wavelength region of 550 to 700 nm.

10. The method according to claim 8, wherein
the fluorescent label has an emission wavelength in a wavelength region of 590 to 650 nm.

11. The method according to claim 8, wherein
the fluorescent label has an emission wavelength in a wavelength region of 590 to 630 nm.

12. The method according to claim 1, wherein the staining reagent comprises eosin.

13. The method according to claim 2, wherein the staining reagent comprises eosin.

14. The method according to claim 1, wherein the staining reagent is a coloring agent.

15. The method according to claim 1, wherein the staining reagent stains the pathological section blue or red.

16. The method according to claim 1, wherein the staining reagent is not used to observe fluorescence emitted therefrom.

17. The method according to claim 1, wherein the fluorescent label comprises a fluorescent nanoparticle comprising phosphor or a semiconductor.

18. The method according to claim 17, wherein the fluorescent nanoparticle has a particle size of 10 to 200 nm.

* * * * *